US005494667A

United States Patent [19]

Uchida et al.

[11] Patent Number: 5,494,667

[45] Date of Patent: Feb. 27, 1996

[54] TOPICALLY APPLIED HAIR RESTORER CONTAINING PINE EXTRACT

[75] Inventors: Yukio Uchida; Satoshi Iritani; Toshio Miyake, all of Okayama, Japan

[73] Assignees: Kabushiki Kaisha Hayahibara; Seibutsu Kagaku Kenkyujo, Okayama, Japan

[21] Appl. No.: 255,897

[22] Filed: Jun. 7, 1994

Related U.S. Application Data

[63] Continuation-in-part of Ser. No. 43,770, Apr. 6, 1993, abandoned.

[30] Foreign Application Priority Data

Jun. 4, 1992 [JP] Japan .................................... 4-185620

[51] Int. Cl.$^6$ ..................................................... A61K 35/78

[52] U.S. Cl. ...................................... 424/195.1; 424/196.1

[58] Field of Search ............................... 424/195.1, 196.1

[56] References Cited

FOREIGN PATENT DOCUMENTS 665257 12/1965 Belgium .

2318620 2/1977 France .

OTHER PUBLICATIONS

JP1218562 Abstract 1989.

JP6128209 Abstract 1986.

Izuno; *Specific Remedy for Athlete's Foot and Psoriasis*, vol. 1, No. 59, 17 Sep. 1982.

Yoshio; *Preparation of Nourishing Skin Lotion From Japanese-Apricot Extract*, vol. 6, No. 257, 12 Feb. 1977.

*Primary Examiner*—John W. Rollins
*Attorney, Agent, or Firm*—Browdy and Neimark

[57] ABSTRACT

A pine extract combined with a bamboo extract and/or a Japanese apricot extract effectively promotes the growth and regeneration of hair for human and animals. Administration of these compounds leads to no substantial side effects. The topically applied hair restorer containing these compounds is also effective in the prevention of alopecias, as well as in the protection of falling out of hair, dandruff, and itching of the scalp. These properties render these compounds useful in hair restorers for human and animals.

17 Claims, No Drawings

TOPICALLY APPLIED HAIR RESTORER CONTAINING PINE EXTRACT

This application is a continuation-in-part, of application Ser. No. 08/043,770, filed Apr. 6, 1993, now abandoned.

BACKGROUND OF THE INVENTION

1. Field of the Invention

The present invention relates to a topically applied hair restorer containing a pine extract and having an augmented effect of the growth and regeneration of hair.

2. Description of the Prior Art

The present inventors have discovered an orally administrable hair restorer containing the extract of a pine, bamboo and Japanese apricot as disclosed in Japanese Patent Application No. 126,605/92.

As described in the thirty-fourth volume of "Pine", the section of tree, "Honzokoumoku", a Chinese medicinal herb guidebook, it is well known that a pine extract has been used for a long time as a hair restorer. Recently, for instance, a hair restorer utilizing a pine extract was disclosed in Japanese Patent Laid-Open No. 164,811/90.

However, the present inventors studied and found that a satisfactory effect of the growth and regeneration of hair is unattainable by using only a pine extract and a topically applied hair restorer is hard to be established by the same. It has been a great demand to establish a highly-safe and topically applied hair restorer containing a pine extract as well as exhibiting an excellent effect of the growth and regeneration of hair.

It would be one of our common wishes to keep our head with capilli during our life.

SUMMARY OF THE INVENTION

The present invention has an object to provide a highly-safe and topically-applied hair restorer containing a pine extract and exhibiting an excellent effect on the growth and regeneration of hair which is applicable to human and animals.

The present invention was made to overcome the above object. The present inventors studied to establish topically applied hair restorer containing a pine extract and having an augmented effect of said pine extract by incorporating in it various plant extracts which have been used as a folk medicine.

As a result, we unexpectedly found that the present object is attainable by incorporating into a pine extract either a or both of a bamboo extract and a Japanese apricot extract which exhibits hardly per se an effect of the growth and regeneration of hair, and accomplished the present invention.

We found that topically applied hair restorer containing a pine extract in a concentration of at least 0.01 w/w % (the wording "w/w %" as referred to in the invention will be abbreviated as "%" hereinafter, unless specified otherwise) and a bamboo extract and a Japanese apricot extract in the range of 0.1 to 100 fold that of the pine extract, respectively on a dry solid basis (d.s.b.), is desirable, and accomplished the present invention.

Furthermore, we found that the effect of the growth and regeneration of hair of said topically applied hair restorer is augmented by incorporating one or more of a member selected from the group consisting of α-glycosyl-L-ascorbic acid, α-glycosyl-bioflavonoid, propolls extract and cyanine dyes, in addition to a pine extract and either or both of a bamboo extract and a Japanese apricot extract.

DETAILED DESCRIPTION OF THE INVENTION

The present invention will be described in detail hereinafter. The pine extracts usable in the invention include those which are prepared by extracting leaves, branches, seeds, cones and barks of pines, as well as their tissue cultures. The extraction is not restricted, and conventional techniques can be suitable employed.

For example, conventional methods as disclosed in Japanese Patent Laid-Open Nos. 21,060/88 and 238,532/89 are suitably employed in the present invention. The former discloses a method for preparing a pine extract comprising extracting pine leaves and trunks with water or an aqueous solution of a readily water-soluble organic solvent such as a lower alcohol or ketone while heating the extraction mixture, and recovering the resultant extract. The latter discloses a method comprising breaking shells of pine cones into pieces, extracting the resultant pieces with an aqueous alkaline solution of an organic base, inorganic base or ammonia, and recovering the resultant extract.

If necessary, a method as disclosed in Japanese Patent Laid-Open No. 172,096/88 can be used to prepare a pine extract for use in the present invention. This method comprises extracting leaves, branches, and/or trunks of pine trees with a liquified carbon dioxide in a sub- or super-critical state at a pressure of from 60–300 $kg/cm^2$ and at 25°–60° C., and recovering the resultant extract. The pine extracts thus obtained may be in the form of a liquid, paste or powder. The form of the extract used can be chosen in light of their final use. Commercially available pine extracts can be used in the present invention.

A commercially available pine extract marketed in Japan under the name SHO-JU-Sen contains as an effective ingredient a pine extract consisting of essential oils such as piniene, camphene, phellandrene, borneol, etc; amino acids such as tryptophane, lysine, histidine, arginine, aspartic acid, threonine, glutamic acid, proline, glycine, alanine, cystine, valine, methionine, isoleucine, leucine, phenylalanin, GABA (gamma amino butyric acid), etc; and organic acids such as tannic acid, shikimic acid and quinine acid. This product is produced by KABUSHIKI-KAISHA WAKANYAKU-KENKYUJO, Tokyo, Japan.

Bamboo extracts which can be used in the present invention are not restricted to any specific type of bamboo extract as long as they contain the active ingredients thereof and exhibit their inherent activities. Examples of such extracts are those which are prepared by conventional methods comprising extracting leaves, branches and roots of bamboo plants, including grass bamboos, and recovering the resultant extracts. The extraction methods are the conventional extraction methods used to prepare pine extracts as described above.

Commercially available sasa extract or extract of bamboo grasses such as concentrated extract of "kumazasa" (plants of the species Sasa albo-marginata), prepared by extracting "kumazasa" with hot water and concentrating the extracts, can be advantageously used. One such product is Hoshi's Striped Bamboo extract, which is prepared by extracting fresh bamboo leaves with hot water.

Any commercially available or conventionally obtained Japanese apricot extracts can be used in the present invention, as long as these extract contain the active ingredients thereof and exhibit their inherent activities. Examples of such extracts are those which an be prepared by conventional methods, including extracting the flesh of the Japanese apricot and recovering the resultant extracts. Conventional extraction methods, such as those described above for obtaining pine extracts, can be used. Commercially available Japanese apricot extracts such as those sold as food products can conveniently be used in the present invention.

A Japanese apricot extract produced by KABUSHIKI-KAISHA MEITAN HONPO, 566 Osaka, Japan, is accompanied by a brochure which contains the following information:

Japanese apricot extract is a Japanese traditional food prepared by squeezing the juice from fresh Japanese apricot and boiling the resulting juice for a relatively long period of time to obtain an extract. The extract is a pure Japanese extract free of salt, so that users who are restricted in their salt intake can taste this extract freely.

Product name: Japanese apricot extract food

Material: Japanese apricot

Net: 90 g

Date of preparation: Indicated below the package

Ingredients: Organic acid in terms of citric aside: 45%

Water: 12–20%

Proteins: 4–10%

Lipids: 0.1–0.5%

Carbohydrates: 70–80%

Ash: 4–7%

Directions: 3 g/day

The α-glycosyl-L-ascorbic acid, α-glycosyl-bioflavonoid and cyanine dyes usable in the present invention are compounds such as those disclosed in Japanese Patent Laid-Open No. 46,112/92, particularly α-glycosyl-L-ascorbic acid, which has a structure consisting of one or more α-D-glucosyl residues bound in a-1,4 fashion to the hydroxyl group at the C-2 position in L-ascorbic acid, as disclosed in Japanese Laid-open Nos. 135,992/91 and 139, 288/91.

The α-glycosyl bioflavonoids such as α-glycosyl rutin, α-glycosyl hesperidin and α-glycosyl naringin usable in the present invention have a structure in which equimolar or more D-glucose residues are bound in e-fashion to bioflavonoids such as rutin, hesperidin and naringin as disclosed in Japanese Patent Laid-Open Nos. 27,293/91; 115,292/91; 7,593/91 and 13,691/92. Japanese Patent Laid-Open Nos. 27,293/91 and 115,292/91 disclose a method for preparing αe-glycosyl rutin by allowing a saccharide-transferring enzyme to act on a solution containing rutin and an amylaceous substance, and recovering the resultant α-glycosyl rutin.

Japanese Patent Laid-Open No. 7,593/91 discloses a method for preparing α-glycosyl hesperidin comprising allowing a saccharide-transferring enzyme to act on a solution containing hesperidin and an α-glucosyl saccharide, and recovering the resultant α-glycosyl hesperidin.

Japanese Patent Laid-Open No. 13,691/91 discloses a method for preparing α-glycosyl naringin comprising allowing a saccharide-transferring enzyme to act on a solution containing naringin and α-glucosyl saccharide, and recovering the resultant α-glucosyl naringin.

Alpha-glycosyl rutin, water-soluble rutin, is a natural food additive whose water solubility is enhanced up to about 5000-fold without adversely affecting the conventional valuable attributes of rutin. Rutin is conventionally used to activate blood vessels. Rutin, otherwise known as Vitamin P, is mainly found in plants such as buckwheat leaves, tomatoes, and figs. Rutin exhibits many useful features, such as absorption of ultraviolet radiation, oxidation inhibition, improving colorfastness, and improving colors.

Alpha-glycosyl rutin is prepared by allowing an enzyme to act on a rutin extract or on a partially hydrolyzed rutin extract. The effective ingredient is known as α-glycosyl rutin.

As disclosed in the International. *J. Vit. Nutr. Res.* 62, 318–323, 1992, ascorbic acid 2-O-α-glucoside is prepared by an enzymatic regioselective transglucosylation. Ascorbic acid 2-O-α-glucoside has been found to be bioavailable as an ascorbate source in vivo.

As reported by Muto et al., in J. Biochem. 107, 222–227, 1990, some mammalian tissue homogenates can catalyze a transglucosylation from maltose to L-ascorbic acid, resulting in a chemically stable derivative of L-ascorbic acid. The cyanine dyes favorably usable in the invention are, for example, the photosensitizing dye "Kankoh-Shikiso No. 301 and Kankoh-Shikiso No. 401" commercialized by Nippon Kankoh-Shikiso Kenkyusho Co., Okayama, Japan.

The propolis extracts usable in the invention include those in liquid form which are prepared by extracting propolis into a readily water-soluble organic solvent such as ethanol in the form of liquid and in the powder form thereof, for example, propolis extracts as disclosed in Japanese Patent Application No. 166,538/91 and 296,698/91 can be advantageously used.

The external-usable hair restorer containing a pine extract of the invention are an external-usable hair restorer containing either or both of a bamboo extract and a Japanese apricot extract together with a pine extract and exhibiting an effect of the growth and regeneration of hair.

The suitable amount of a pine extract is at least 0.01%, preferably, in the range of 0.02 to 5%. In case that the amount of a pine extract is less than 0.01%, the inherent effect of the pine extract would be expected, while said effect is deteriorated by a bamboo extract and a Japanese apricot extract when the amount of the pine extract exceeds 5%, d.s.b. Neither a bamboo extract nor a Japanese apricot extract exhibits per se an effect of the growth and regeneration of hair, however said effect is extremely exhibited and augmented in combination with a pine extract. The amounts of a bamboo extract and a Japanese apricot extract against that of a pine extract suitably used in the invention are respectively about 0.1 to 100 fold, d.s.b., preferably, in the range of about 0.1 to 20 fold, d.s.b. for the augmentation of the effect of the growth and regeneration of hair.

The amounts of α-glycosyl ascorbic acid, α-glycosyl bioflavonoid and propolis extract against that of a pine extract suitably used in the invention are respectively in the range of about 0.1 to 100.0 fold, d.s.b.

The amounts of cyanine dyes against that of a pine extract suitably used in the invention is in the range of about 0.01 to 1.0 fold, d.s.b.

The external-usable hair restorer of the invention is preferably adjusted to an aqueous solution containing the above essential ingredients totally in a concentration of about 0.1 to 30%, desirably in the range of about 0.5 to 20%. The hair restorer can be advantageously adjusted into an adequate concentration depending on sort of the ingredients to be incorporated and of hair diseases to be treated, if necessary, and the hair restorer can be prepared into an adequate form, for example, in liquid, jelly, emulsion, aerosol or paste.

In addition to the above essential ingredients, for example, an oil- or water-base, emollient, emulsifier, gelatinizer, flavoring agent, antiseptic, antioxidant, coloring agent, refrigerant, bactericide, humectant and pH adjuster, which have been used in conventional hair restorers, can be suitably incorporated in the present hair restorer, if necessary.

Furthermore, the present hair restorer can be used in combination with other ingredients, for example, vitamins, hormones, amino acids, vasodilator, blood-circulation promoting agents, cell activators, antiinflammatories, hyperergic agents for skin, and keratolytic, which have an effect of the growth and regeneration of hair.

The external-usable hair restorer according to the present invention is used as an adequate hair-care product, for example, hair restorer, hair tonic, hair liquid, hair lotion, hair cream, hair oil, hair treatment, hair mousse, shampoo, rinse and oniment. The hair restorer of the invention is commercially valuable because it remains stable over a relatively long period of time, and is excellent in the promotion of the growth and regeneration of hair when applied to human skin.

Thus, the present external-usable hair restorer accelerates the growth and regeneration of hair and improves the symptom of alopecias, for example, juvenile alopecia, premature alopecia, senile alopecia, alopecia areata, mechanical alopecia, and symptomatic alopecia, as well as exhibiting a satisfactory preventive and therapeutic effect on dandruff, poliosis, and itching of the scalp or skin.

Furthermore, the present hair restorer imparts a commercial value to fur-animals such as sheep, fox, alpaca, angora rabbit, mink and cashmere goat whose hair and fur are utilized. The hair restorer can be utilized for improving the quality of hair or plumage of pet animals such as dog, cat, parakeet and canary, and enriching the hair gloss of such animals.

The present topically applied hair restorer is usually administered 1 to 3 times a day to hair sites.

If necessary, the effect of the growth and regeneration of hair can be more augmented by iontophoresing an ionized solution of the ingredients into affected sites with the low-frequency therapeutic apparatuses such as disclosed in Japanese Patent Publication No. 41,747/84 and Japanese Patent Laid-Open No. 56,060/89.

The following experiments will explain the present invention in detail.

Experiment 1

Influence of plant extracts on effect of the growth and regeneration of hair of pine extract The effect of the growth and regeneration of hair of pine extracts and plant extracts as well as the mixture thereof was evaluated.

The pine extract was in usual manner prepared from a pine leaf and other plant extracts were prepared from commercially available ones or prepared in usual manner, respectively dissolved to give a concentration of 1.0% in a 50.0% aqueous ethanol solution containing 2.0% propyleneglycol. The resultant was adjusted to pH 6.7 by the addition of hydrochloric acid or sodium hydroxide to obtain a solution in hair lotion form. As a control, a solution in hair lotion form was prepared similarly as above, except that the plant extracts were replaced with refined water.

The dorsum surface of rabbits was sectioned into four areas, 5 $cm^2$ each, i.e. two areas near the head end and two areas near the tail end which were respectively bisymmetrical about the vertebral columns of the rabbits, the four areas were depilated by applying thereto silver cream and subjecting them to brief standing. The depilated areas were first sufficiently washed with water, then the depilated areas of the right area near the head end, the left area near the head end, and the right area near at tail end were respectively applied once every day by using a paintbrush with 1 ml of the test solution containing only an extract, 1 ml of the control solution containing refined water, and 1 ml of the test solution containing the mixture of extracts. Furthermore, the left area near the tail end was untreated.

The application of each solution was started on the second day after the depilation, and the newly regenerated hairs were depilated to count on the 10th and 20th days after the application. The length of 10 coarse hairs regenerated in each area was measured with a micromanipulator, and expressed by the mean remainder of hair length (mm) between the hair length in the area which had been applied with a sample solution and that in the area which had been untreated.

In addition, it has been known that the growth rates of hairs in the bisymmetrical dorsum surface about the vertebral column of rabbit is in the same level, and those in both sexes are also in the same level.

The results were as shown in Table 1.

As evidence from the results in Table 1, a synergistic improvement of the effect of the growth and regeneration of hair was found in the groups of the areas

TABLE 1

| Test No. | | Mean remainder of hair length (mm) 10th | 20th |
|---|---|---|---|
| 1. | Pine extract | 0.3 | 0.5 |
| 2. | Pine extract + loquat (*Eriobotrya japonica*) leaf extract | 0.1 | 0.1 |
| 3. | Dokudami (*Houttuynia cordata*) extract | 0.1 | 0.1 |
| 4. | Chlorella extract | 0.1 | 0.1 |
| 5. | Bamboo extract | 0.1 | 0.2 |
| 6. | Suzuna (*Arabis flagellosa Miq.*) extract | 0.1 | 0.1 |
| 7. | Japanese apricot extract | 0.1 | 0.2 |
| 8. | Pine extract + loquat leaf extract | 0.2 | 0.5 |
| 9. | Pine extract + dokudami extract | 0.3 | 0.6 |
| 10. | Pine extract + chlorella extract | 0.3 | 0.5 |
| 11. | Pine extract + bamboo extract | 0.5 | 1.0 |
| 12. | Pine extract + suzuna extract | 0.3 | 0.5 |
| 13. | Pine extract + Japanese apricot extract | 0.6 | 1.1 |
| 14. | Refined water | 0.0 | 0.0 |

which had been treated with the sample solution containing pine extracts in combination with bamboo extracts and Japanese apricot extracts.

Experiment 2

Influence of bamboo extract and Japanese apricot extract on an effect of the growth and regeneration of hair of pine extract By using the sample solutions containing bamboo extracts and Japanese apricot extracts together with pine extracts, the effect of the growth and regeneration of hair was evaluated by the same method as in Experiment 1.

Samples used in the panel test were prepared by the same method as that in Experiment 1 by first providing a group consisting of 0.02%, 0.2% and 2.0% of a pine extract, then adding to the groups 0.1 to 100 fold volumes of a bamboo extract and a Japanese apricot extract against the weight of the pine extract, respectively d.s.b.

The application term of each solution was extended to 30 days after the depilation, and the newly regenerated hairs were measured on the 20th and 30th days after the application at the same way of Experiment 1, and expressed by the mean remainder of hair length (mm) in between the applied and the untreated area.

The results were as shown in Table 2.

As evidence from the results in Table 2, an extremely great improvement of the effect of the growth and regeneration of hair of a pine extract was found in the groups of the areas which had been treated with the sample solution containing pine extracts in combination with bamboo extracts and Japanese apricot extracts.

TABLE 2

| Test No. | | | Magnification against pine extract, d.s.b. | | Mean remainder of hair lenght (mm) 20th | 30th |
|---|---|---|---|---|---|---|
| 1. | Pine extract 0.02% | + | Bamboo extract | 0 | | |
| | | | Japanese apricot extract | 0 | 0.1 | 0.2 |
| 2. | Pine extract 0.02% | + | Bamboo extract | 10.0 | | |
| | | | Japanese apricot extract | 10.0 | 0.3 | 0.5 |
| 3. | Pine extract 0.02% | + | Bamboo extract | 100.0 | | |
| | | | Japanese apricot extract | 100.0 | 0.6 | 0.7 |
| 4. | Pine extract 0.2% | + | Bamboo extract | 0 | | |
| | | | Japanese apricot extract | 0 | 0.3 | 0.4 |
| 5. | Pine extract 0.2% | + | Bamboo extract | 1.0 | | |
| | | | Japanese apricot extract | 1.0 | 1.1 | 1.7 |
| 6. | Pine extract 0.2% | + | Bamboo extract | 10.0 | | |
| | | | Japanese apricot extract | 10.0 | 1.5 | 1.9 |
| 7. | Pine extract 2.0% | + | Bamboo extract | 0 | | |
| | | | Japanese apricot extract | 0 | 0.7 | 0.8 |
| 8. | Pine extract 2.0% | + | Bamboo extract | 0.1 | | |
| | | | Japanese apricot extract | 0.1 | 1.5 | 2.0 |
| 9. | Pine extract 2.0% | + | Bamboo extract | 1.0 | 1.8 | 2.2 |
| | | | Japanese apricot extract | 1.0 | | |
| 10. | Refined water | | | | 0.0 | 0.0 |

Experiment 3

Clinical test

By using the No. 6 and No. 8 specimens which had been demonstrated a satisfactory effect of the growth and regeneration of hair in Experiment 2, volunteers with alopecia participated in a 3-month clinical test. As a control, the No. 10 specimen prepared by the method in Experiment 2 was used. The volunteers were 20 randomly chosen patients with alopecias (10 men and 10 women) who were 18 to 62 years old.

The symptoms of the volunteers, who had received a pharmacotherapy or physiotherapy at a department of dermatology, were male alopecia such as juvenile alopecia, premature alopecia, senile alopecia, and alopecia areata such as multiple alopecia areata and malignant alopecia areata.

Since the symptoms of the volunteers with a slight alopecia areata may spontaneously recover, the volunteers with a relatively small alopecic site and those with atrophia cutis or atrophic pores which were not clinically observed were excluded from this Experiment.

The procedure of therapeutic treatment used in this Experiment is carried out by applying to the affected sites of the volunteers a thin coat of the hair restorer, massaging the sites sufficiently and exposing the sites to an artificial sunlight. Furthermore the volunteers were instructed to apply the hair restorer to the affected sites 3 times a day at home.

The efficacy of the growth and regeneration of hair attained by the hair restorer was evaluated based on the four ranks, i.e. "recovery (hair was newly regenerated to exhibit an area apparently free from alopecia)", "moderate recovery (though the rate of hair regeneration was moderate, no recurrence of alopecia was found)", "not affected (no regeneration of hair was found)", and "unfavorable (side effect or the acceleration of alopecia was found)".

The results were as shown in Table 3.

As evident from the results in Table 3, similar to the animal test in Experiment 2, the sample solution containing pine extracts together with bamboo extracts and Japanese apricot extracts exhibited an extremely great improvement of the effect of the growth and regeneration of hair, and exhibited a satisfactory therapeutic effect against various alopecias. Furthermore, no side effect of the sample solution was found.

Experiment 4

Acute toxicity test

Samples No. 11 and No. 13 prepared by the method in Experiment 1 and samples No. 3, No. 6 and No. 9 prepared by the method in Experiment 2 were tested for the acute toxicity by administering respectively the samples to 7-week-old dd-strain mice.

No mouse died up to the dose of 5 g/rat, and a higher dose test was impossible. The results revealed that the acute toxicities of the samples were extremely low.

The preferred examples of the present invention will be described hereinafter.

TABLE 3

| Effective ingredients | | Therapeutic efficacy (Mumber of volunteers) Recovery | Moderate recovery | Not affected | Unfavorable | Judgement |
|---|---|---|---|---|---|---|
| Pine extract | 0.2% | | | | | |
| Bamboo extract | 2.0% | | | | | |
| Japanese apricot extract | 2.0% | 4 | 12 | 4 | 0 | Present Invention |
| Pine extract | 2.0% | | | | | |
| Bamboo extract | 0.2% | | | | | |
| Japanese apricot extract | 0.2% | 6 | 11 | 3 | 0 | Present Invention |
| Refined water | | 0 | 3 | 15 | 2 | Control |

Example 1

Hair tonic

Fifty-five parts by weight of ethanol, 2.0 parts of weight of polyoxyethylene (8) oleyl alcohol ether, 35 parts by weight of refined water, 3.0 parts by weight of a pine extract (about 20% concentration), 3.0 parts by weight of a bamboo extract (about 25% concentration), 2.0 parts by weight of a Japanese apricot extract (about 45% concentration), in addition, an adequate amounts of β-thujaplicin (hinokitiol), flavoring agent and coloring agent were mixed in usual manner to obtain a hair restorer in hair tonic form. The present product can be advantageously used in the promotion of the growth and regeneration of hair, as well as in the treatment and prevention of falling out of hair, dandruff, and itching of the scalp or skin.

The product can be also used as a hair tonic because the product exhibits an effect of imparting flavor and refreshment.

In addition, the product can be advantageously used as a preventive or traumatherapeutic agent for the scalp because the product exerts an effect of bactericidal and antiphlogistic activity.

Example 2

Hair tonic

Five parts by weight of powdery pine extract, 2.5 parts by weight of bamboo extract (about 40% concentration), 2.0 parts by weight of α-glycosyl rutin ("αG rutin" commercialized by Toyo Sugar Refining Co., Ltd., Japan) and 20.0 parts by weight of glycerin were added to 550 parts by weight of refined water (60° C.). To the mixture thus obtained was further added a solution containing 0.05 parts by weight of cyanine dyes ("Kankoh-Sikiso No. 301") and 440 parts by weight of ethanol, and a solution containing 2.0 parts by weight of L-menthol, 1.0 part by weight of propolls extract (15% concentration) and 10 parts by weight of ethanol, and the mixture mixed and filtered in the usual manner and thereafter injected into a bottle to obtain a hair restorer in hair tonic form.

The present product can be advantageously used in the promotion of the growth and regeneration of hair, as well as in the treatment and prevention of falling out of hair, dandruff, and itching of the scalp or skin.

In addition, the product can be advantageously used as a preventive or traumatherapeutic agent for the scalp because the product exerts an effect of bactericidal and antiphlogistic activity.

Example 3

Hair liquid

Fifty-five parts by weight of ethanol, 20.0 parts by weight of polyoxyethylene (40) butyl ether, 13 parts by weight of refined water, 5.0 parts by weight of pine extract (about 20% concentration), 5.0 parts by weight of Japanese apricot extract (about 45% concentration) and 3.0 parts by weight of 2-O-α-D-glucopyranosyl-L-ascorbic acid, in addition, an adequate amounts of pH adjuster, flavoring agent and antiseptic, the resultant mixture were mixed to obtain a hair restorer in hair liquid form.

The present product can be advantageously used in the promotion of the growth and regeneration of hair, as well as in the treatment and prevention of falling out of hair, dandruff, and itching of the scalp or skin.

In addition, the present product can be advantageously used as a preventive or traumatherapeutic agent for the scalp because the product exerts an bactericidal and antiphlogistic activity.

Example 4

Hair cream

Three parts by weight of beeswax, 15.0 parts by weight of petrolatum, 42.0 parts by weight of liquid paraffin, 3.0 parts by weight of polyoxyethylene (5) ester stearate, 2.0 parts by weight of polyoxyethylene (6) oleyl alcohol ether, 1.0 part by weight of polyoxyethylene (6) cetyl alcohol ether, 1.0 part of weight of powdery pine extract, 1.5 parts by weight of bamboo extract (about 40% concentration), 1.0 part of weight of Japanese apricot extract (about 85% concentration), 0.2 parts by weight of a-glycosyl rutin, 0.3 parts by weight of 2-O-α-D-glucopyranosyl-L-ascorbic acid and 32 parts by weight of refined water, in addition, an adequate of pH adjuster, flavoring agent and antiseptic, were mixed to obtain a hair restorer in hair cream form.

The present product can be advantageously used in the promotion of the growth and regeneration of hair, as well as in the treatment and prevention of falling out of hair, dandruff, and itching of the scalp or skin.

In addition, the product can be advantageously used as a hair cream because the product imparts a gloss to hair, as well as supplementing nutrition to the skin and exerting an antiphlogistic activity.

Example 5

Ointment

Ten parts by weight of anionic auto-emulsified wax, 3.0 parts by weight of myristic acid isopropyl, 3.0 parts by weight of liquid paraffin, 4.0 parts by weight of cetanol, 5.0 parts by weight of maltose, 10.0 parts by weight of propolls extract (about 10% concentration), 2.0 parts by weight of a powdery pine extract, 2.0 parts by weight of a bamboo extract (about 20% concentration), 1.0 part by weight of a Japanese apricot extract (about 45% concentration), 1.0 part by weight of a-glycosyl rutin, 51.0 parts by weight of refined water, and an adequate amounts of antiseptic were mixed to obtain a hair restorer in oniment form.

The present product can be advantageously used in the promotion of the growth and regeneration of hair, as well as in the treatment and prevention of falling out of hair, dandruff, and itching of the scalp or skin.

In addition, the present product can be advantageously used as a preventive or traumatherapeutic agent for the scalp because the product exerts an bactericidal and antiphlogistic activity.

Effects of the invention

As described above, the present invention establishes a topically applied hair restorer by incorporating into a pine extract either or both of a bamboo extract and a Japanese apricot extract, and augments extremely an effect of the growth and regeneration of hair which a pine extract exhibits. The present invention has an industrial advantage in the treatment and prevention of alopecia and falling out of hair as well as in the beauty culture and cosmetics. Furthermore, the present invention advantageously contributes for improving the growth and regeneration of hair or plumage of domestic animals and the quality of hair or plumage of pet animals.

While there has been described what is at present considered to be the preferred embodiments of the invention, it will be understood that various modifications may be made therein, and it is intended to cover the appended claims all such modifications as fall within the true spirit and scope of the invention.

We claim:

1. In a topically applied hair restorer for topical application to hair sites of animals comprising a pine extract as effective ingredient, the improvement comprising incorporating at least 0.01 w/w% of a pine extract in said hair restorer together with a member selected from the group consisting of bamboo extracts, Japanese apricot extracts, and mixtures thereof, in an amount of 0.1 to 100 fold of that of the pine extract, whereby the growth and regeneration of hair in the sites are accelerated, and the symptoms of an alopecia selected from the group consisting of juvenile alopecia, premature alopecia, senile alopecia, alopecia areata, mechanical alopecia, and symptomatic alopecia are improved.

2. In an method for accelerating the growth and regeneration of hair and reducing the symptoms of alopecia in an animal, the improvement comprising applying to the affected area of said animal an effective amount of the hair restorer of claim 1.

3. The topically applied hair restorer of claim 1, further containing at least one member selected from the group consisting of α-glycosyl-L-ascorbic acid, α-glycosyl-bioflavonoid and propolis extracts.

4. The topically applied hair restorer of claim 3, wherein said α-glycosyl-L-ascorbic acid is selected from the group consisting of 2-O-α-D-glucosyl-L-ascorbic acid, 2-O-α-maltosyl-L-ascorbic acid, 2-O-α-maltotriosyl-L-ascorbic acid, 2-O-α-maltotetraosyl-L-ascorbic acid, 2-O-α-maltopentaosyl-L-ascorbic acid, 2-O-α-maltohexaosyl-L-ascorbic acid, 2-O-α-maltoheptaosyl-L-ascobic acid, and mixtures thereof.

5. The topically applied hair restorer of claim 3, wherein said α-glycosyl-bioflavonoid is selected from the group consisting of α-glycosyl rutin, α-glycosyl hesperidin, α-glycosyl naringin, and mixtures thereof.

6. The topically applied hair restorer of claim 5, wherein said α-glycosyl rutin is selected from the group consisting of α-glucosyl rutin, α-maltosyl rutin, α-maltotriosyl rutin, α-maltotetraosyl rutin, α-maltopentaosyl rutin, and mixtures thereof.

7. The topically applied hair restorer of claim 5, wherein said α-glycosyl hesperidin is selected from the group consisting of α-glucosyl hesperidin, α-maltosyl hesperidin, α-maltotriosyl hesperidin, α-maltotetraosyl hesperidin, α-maltopentaosyl hesperidin, and mixtures thereof.

8. The topically applied hair restorer of claim 5, wherein said α-glycosyl naringin is a member selected from the group consisting of α-glucosyl naringin, α-maltosyl naringin, α-maltotriosyl naringin, α-maltotetraosyl naringin, and mixtures thereof.

9. The topically applied hair restorer of claim 3, which the respective amount of said at least one additional ingredient is from about 0.1 to 100 times that of said pine extracts, on a dry solid basis.

10. The topically applied hair restorer of claim 1, further containing cyanine dyes in an amount of about 0.01 to 1.0 fold of that of said pine extracts on a dry solid basis.

11. The topically applied hair restorer of claim 1, wherein the topically acceptable carrier is in the form of liquid, jelly, emulsion, aerosol or ointment.

12. The topically applied hair restorer of claim 1, which further contains an effective amount of humectant.

13. The topically applied hair restorer of claim 12, wherein said humectant is selected from the group consisting of propyleneglycol, glycerine and polyoxyethylene glycol.

14. A method for restoring hair to an animal in need thereof, which animal exhibits symptoms of an alopecia selected from the group consisting of juvenile alopecia, premature alopecia, senile alopecia, alopecia areata, mechanical alopecia, and symptomatic alopecia comprising applying topically one to three times a day to the affected hair sites of the animal an effective amount to restore hair at said hair sites of the topically applied hair restorer according to claim 1.

15. The method according to claim 14 wherein the animal is a human.

16. A method for restoring hair to an animal in need thereof, which animal exhibits symptoms of an alopecia selected from the group consisting of juvenile alopecia, premature alopecia, senile alopecia, alopecia areata, mechanical alopecia, and symptomatic alopecia comprising applying topically one to three times a day to the affected hair sites of the animal an effective amount to restore hair at said hair sites of the topically applied hair restorer according to claim 3.

17. The method according to claim 16 wherein the animal is a human.

* * * * *